(12) United States Patent
Song

(10) Patent No.: US 7,781,172 B2
(45) Date of Patent: *Aug. 24, 2010

(54) METHOD FOR EXTENDING THE DYNAMIC DETECTION RANGE OF ASSAY DEVICES

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 900 days.

This patent is subject to a terminal disclaimer.

(21) Appl. No.: 10/719,976

(22) Filed: Nov. 21, 2003

(65) Prior Publication Data

US 2005/0112780 A1    May 26, 2005

(51) Int. Cl.
| | |
|---|---|
| C12Q 1/68 | (2006.01) |
| C12Q 1/00 | (2006.01) |
| G01N 15/06 | (2006.01) |
| G01N 21/00 | (2006.01) |
| G01N 33/53 | (2006.01) |
| G01N 33/566 | (2006.01) |
| G01N 33/543 | (2006.01) |
| G01N 33/544 | (2006.01) |
| B01L 3/00 | (2006.01) |
| C12M 1/34 | (2006.01) |
| C12M 3/00 | (2006.01) |

(52) U.S. Cl. ............................ 435/7.1; 422/50; 422/55; 422/56; 422/58; 422/61; 422/68.1; 435/4; 435/287.1; 435/287.2; 435/287.7; 435/288.7; 436/501; 436/518; 436/528; 436/530

(58) Field of Classification Search .................. 422/50, 422/55, 56, 58, 61, 68.1; 435/4, 7.1, 287.1, 435/287.2, 287.7, 288.7; 436/501, 518, 528, 436/530
See application file for complete search history.

(56) References Cited

U.S. PATENT DOCUMENTS 1,366,241 A    1/1921    Burch
(Continued)

FOREIGN PATENT DOCUMENTS

EP    0073593 A1    3/1983
(Continued)

OTHER PUBLICATIONS

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

(Continued)

*Primary Examiner*—Gailene R Gabel
*Assistant Examiner*—Jacqueline Diramio
(74) *Attorney, Agent, or Firm*—Dority & Manning, P.A.

(57) ABSTRACT

A flow-through assay device for detecting the presence or quantity of an analyte residing in a test sample is provided. The device utilizes a detection zone and compensation zone within which are immobilized capture reagents. The present inventor has discovered that the presence of a compensation zone may enable the detection of an analyte over extended concentration ranges. In particular, the compensation zone facilitates the binding of probes that would otherwise bind within the interior of assay device or that would exhibit "self-quenching".

18 Claims, 4 Drawing Sheets

U.S. PATENT DOCUMENTS

| | | |
|---|---|---|
| 3,700,623 A | 10/1972 | Keim |
| 3,772,076 A | 11/1973 | Keim |
| 4,094,647 A | 6/1978 | Deutsch et al. |
| 4,110,529 A | 8/1978 | Stoy |
| 4,115,535 A | 9/1978 | Giaever |
| 4,168,146 A | 9/1979 | Grubb et al. |
| RE30,267 E | 5/1980 | Bruschi |
| 4,210,723 A | 7/1980 | Dorman et al. |
| 4,235,601 A | 11/1980 | Deutsch et al. |
| 4,275,149 A | 6/1981 | Litman et al. |
| 4,312,228 A | 1/1982 | Wohltjen |
| 4,363,874 A | 12/1982 | Greenquist |
| 4,366,241 A | 12/1982 | Tom et al. |
| 4,374,925 A | 2/1983 | Litman et al. |
| 4,385,126 A | 5/1983 | Chen et al. |
| 4,426,451 A | 1/1984 | Columbus |
| 4,427,836 A | 1/1984 | Kowalski et al. |
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,657 A | 8/1985 | Keim |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,586,695 A | 5/1986 | Miller |
| 4,595,661 A | 6/1986 | Cragle et al. |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A | 10/1987 | Campbell et al. |
| 4,722,889 A | 2/1988 | Lee et al. |
| 4,727,019 A | 2/1988 | Valkirs et al. |
| 4,731,337 A | 3/1988 | Luotola et al. |
| 4,742,011 A | 5/1988 | Blake et al. |
| 4,743,542 A | 5/1988 | Graham, Jr. et al. |
| 4,743,560 A | 5/1988 | Campbell et al. |
| 4,776,944 A | 10/1988 | Janata et al. |
| 4,806,312 A | 2/1989 | Greenquist |
| 4,835,099 A | 5/1989 | Mize et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,867,908 A | 9/1989 | Recktenwald et al. |
| 4,877,586 A | 10/1989 | Devaney, Jr. et al. |
| 4,877,747 A | 10/1989 | Stewart |
| 4,889,816 A | 12/1989 | Davis et al. |
| 4,895,017 A | 1/1990 | Pyke et al. |
| 4,904,583 A | 2/1990 | Mapes et al. |
| 4,916,056 A | 4/1990 | Brown, III et al. |
| 4,917,503 A | 4/1990 | Bhattacharjee |
| 4,920,045 A | 4/1990 | McFarland et al. |
| 4,940,734 A | 7/1990 | Ley et al. |
| 4,954,435 A | 9/1990 | Krauth |
| 4,956,302 A | 9/1990 | Gordon et al. |
| 4,963,498 A | 10/1990 | Hillman et al. |
| 4,973,670 A | 11/1990 | McDonald et al. |
| 4,978,625 A | 12/1990 | Wagner et al. |
| 4,980,298 A | 12/1990 | Blake et al. |
| 4,992,385 A | 2/1991 | Godfrey |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,073,340 A | 12/1991 | Covington et al. |
| 5,075,077 A | 12/1991 | Durley, III et al. |
| 5,075,078 A | 12/1991 | Osikowicz et al. |
| 5,076,094 A | 12/1991 | Frye et al. |
| 5,096,671 A | 3/1992 | Kane et al. |
| 5,114,676 A | 5/1992 | Leiner et al. |
| 5,120,643 A | 6/1992 | Ching et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,145,784 A | 9/1992 | Cox et al. |
| 5,149,622 A | 9/1992 | Brown et al. |
| 5,152,758 A | 10/1992 | Kaetsu et al. |
| 5,156,953 A | 10/1992 | Litman et al. |
| 5,166,079 A | 11/1992 | Blackwood et al. |
| 5,179,288 A | 1/1993 | Miffitt et al. |
| 5,182,135 A | 1/1993 | Giesecke et al. |
| 5,185,127 A | 2/1993 | Vonk |
| 5,196,350 A | 3/1993 | Backman et al. |
| 5,200,084 A | 4/1993 | Liberti et al. |
| 5,208,143 A | 5/1993 | Henderson et al. |
| 5,208,535 A | 5/1993 | Nakayama et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,275,785 A | 1/1994 | May et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,531 A | 12/1994 | Jensen |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,428,690 A | 6/1995 | Bacus et al. |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |

| Patent No. | Date | Inventor |
|---|---|---|
| 5,482,830 A | 1/1996 | Bogart et al. |
| 5,482,867 A | 1/1996 | Barrett et al. |
| 5,484,867 A | 1/1996 | Lichtenhan et al. |
| 5,489,678 A | 2/1996 | Fodor et al. |
| 5,489,988 A | 2/1996 | Ackley et al. |
| 5,492,840 A | 2/1996 | Malmqvist et al. |
| 5,500,350 A | 3/1996 | Baker et al. |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,514,559 A | 5/1996 | Markert-Hahn et al. |
| 5,514,785 A | 5/1996 | Van Ness et al. |
| 5,516,635 A | 5/1996 | Ekins et al. |
| 5,518,689 A | 5/1996 | Dosmann et al. |
| 5,518,883 A | 5/1996 | Soini |
| 5,527,711 A | 6/1996 | Tom-Moy et al. |
| 5,534,132 A | 7/1996 | Vreeke et al. |
| 5,554,539 A | 9/1996 | Chadney et al. |
| 5,554,541 A | 9/1996 | Malmqvist et al. |
| 5,569,608 A | 10/1996 | Sommer |
| 5,571,684 A | 11/1996 | Lawrence et al. |
| 5,573,909 A | 11/1996 | Singer et al. |
| 5,573,919 A | 11/1996 | Kearns et al. |
| 5,585,279 A | 12/1996 | Davidson |
| 5,589,401 A | 12/1996 | Hansen et al. |
| 5,591,581 A | 1/1997 | Massey et al. |
| 5,591,645 A | 1/1997 | Rosenstein |
| 5,596,414 A | 1/1997 | Tyler |
| 5,599,668 A | 2/1997 | Stimpson et al. |
| 5,602,040 A | 2/1997 | May et al. |
| 5,610,077 A | 3/1997 | Davis et al. |
| 5,618,732 A | 4/1997 | Pease et al. |
| 5,618,888 A | 4/1997 | Choi et al. |
| 5,620,850 A | 4/1997 | Bamdad et al. |
| 5,622,871 A | 4/1997 | May et al. |
| 5,637,509 A | 6/1997 | Hemmilä et al. |
| 5,647,994 A | 7/1997 | Tuunanen et al. |
| 5,656,448 A * | 8/1997 | Kang et al. .................. 435/7.94 |
| 5,656,503 A | 8/1997 | May et al. |
| 5,658,443 A | 8/1997 | Yamamoto et al. |
| 5,663,213 A | 9/1997 | Jones et al. |
| 5,670,381 A | 9/1997 | Jou et al. |
| 5,672,256 A | 9/1997 | Yee |
| 5,700,636 A | 12/1997 | Sheiness et al. |
| 5,714,389 A | 2/1998 | Charlton et al. |
| 5,726,064 A | 3/1998 | Robinson et al. |
| 5,731,147 A | 3/1998 | Bard et al. |
| 5,736,188 A | 4/1998 | Alcock et al. |
| 5,753,517 A | 5/1998 | Brooks et al. |
| 5,770,416 A | 6/1998 | Lihme et al. |
| 5,780,308 A | 7/1998 | Ching et al. |
| 5,788,863 A | 8/1998 | Milunic |
| 5,795,470 A | 8/1998 | Wang et al. |
| 5,795,543 A | 8/1998 | Poto et al. |
| 5,798,273 A | 8/1998 | Shuler et al. |
| 5,811,526 A | 9/1998 | Davidson |
| 5,827,748 A | 10/1998 | Golden |
| 5,834,226 A | 11/1998 | Maupin |
| 5,837,429 A | 11/1998 | Nohr et al. |
| 5,837,546 A | 11/1998 | Allen et al. |
| 5,837,547 A | 11/1998 | Schwartz |
| 5,843,692 A | 12/1998 | Phillips et al. |
| 5,852,229 A | 12/1998 | Josse et al. |
| 5,876,944 A | 3/1999 | Kuo |
| 5,885,527 A | 3/1999 | Buechler |
| 5,906,921 A | 5/1999 | Ikeda et al. |
| 5,910,286 A | 6/1999 | Lipskier |
| 5,910,447 A | 6/1999 | Lawrence et al. |
| 5,910,940 A | 6/1999 | Guerra |
| 5,922,537 A | 7/1999 | Ewart et al. |
| 5,922,550 A | 7/1999 | Everhart et al. |
| 5,945,281 A | 8/1999 | Prabhu |
| 5,951,492 A | 9/1999 | Douglas et al. |
| 5,962,995 A | 10/1999 | Avnery |
| 5,968,839 A | 10/1999 | Blatt et al. |
| 5,985,432 A | 11/1999 | Wang et al. |
| 5,989,924 A | 11/1999 | Root et al. |
| 5,989,926 A | 11/1999 | Badley et al. |
| 5,998,221 A | 12/1999 | Malick et al. |
| 6,004,530 A | 12/1999 | Sagner et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,030,840 A | 2/2000 | Mullinax et al. |
| 6,033,574 A | 3/2000 | Siddiqi |
| 6,033,918 A * | 3/2000 | Hatch et al. .................. 436/530 |
| 6,048,623 A | 4/2000 | Everhart et al. |
| 6,057,165 A | 5/2000 | Mansour |
| 6,060,256 A | 5/2000 | Everhart et al. |
| 6,077,669 A | 6/2000 | Little et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,103,537 A | 8/2000 | Ullman et al. |
| 6,117,090 A | 9/2000 | Caillouette |
| 6,121,008 A * | 9/2000 | Fitzpatrick et al. ........... 435/7.9 |
| 6,130,100 A | 10/2000 | Jobling et al. |
| 6,133,048 A | 10/2000 | Penfold et al. |
| 6,136,549 A | 10/2000 | Feistel |
| 6,136,611 A | 10/2000 | Saaski et al. |
| 6,139,961 A | 10/2000 | Blankenship et al. |
| 6,151,110 A | 11/2000 | Markart |
| 6,156,271 A | 12/2000 | May et al. |
| 6,165,798 A | 12/2000 | Brooks |
| 6,171,780 B1 | 1/2001 | Pham et al. |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,183,972 B1 | 2/2001 | Kuo et al. |
| 6,184,042 B1 | 2/2001 | Neumann et al. |
| 6,187,269 B1 | 2/2001 | Lancesseru et al. |
| 6,194,220 B1 | 2/2001 | Malick et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,235,471 B1 | 5/2001 | Knapp et al. |
| 6,235,491 B1 | 5/2001 | Connolly |
| 6,241,863 B1 | 6/2001 | Monbouquette |
| 6,242,268 B1 | 6/2001 | Wieder et al. |
| 6,255,066 B1 | 7/2001 | Louderback |
| 6,261,779 B1 | 7/2001 | Barbera-Guillem et al. |
| 6,268,222 B1 | 7/2001 | Chandler et al. |
| 6,270,637 B1 | 8/2001 | Crismore et al. |
| 6,271,040 B1 | 8/2001 | Buechler |
| 6,274,324 B1 | 8/2001 | Davis et al. |
| 6,281,006 B1 | 8/2001 | Heller et al. |
| 6,284,472 B1 | 9/2001 | Wei et al. |
| 6,287,783 B1 | 9/2001 | Maynard et al. |
| 6,287,871 B1 | 9/2001 | Herron et al. |
| 6,294,391 B1 | 9/2001 | Badley et al. |
| 6,294,392 B1 | 9/2001 | Kuhr et al. |
| 6,306,665 B1 | 10/2001 | Buck et al. |
| D450,854 S | 11/2001 | Lipman et al. |
| 6,331,438 B1 | 12/2001 | Aylott et al. |
| 6,348,186 B1 | 2/2002 | Sutton et al. |
| 6,352,862 B1 | 3/2002 | Davis et al. |
| 6,362,011 B1 | 3/2002 | Massey et al. |
| 6,368,873 B1 | 4/2002 | Chang et al. |
| 6,368,875 B1 | 4/2002 | Geisberg |
| 6,387,707 B1 | 5/2002 | Seul et al. |

| | | |
|---|---|---|
| 6,391,558 B1 | 5/2002 | Henkens et al. |
| 6,399,295 B1 | 6/2002 | Kaylor et al. |
| 6,399,397 B1 | 6/2002 | Zarling et al. |
| 6,399,398 B1 | 6/2002 | Cunningham et al. |
| 6,407,492 B1 | 6/2002 | Avnery et al. |
| 6,411,439 B2 | 6/2002 | Nishikawa |
| 6,413,410 B1 | 7/2002 | Hodges et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,451,607 B1 | 9/2002 | Lawrence et al. |
| 6,455,861 B1 | 9/2002 | Hoyt |
| 6,461,496 B1 | 10/2002 | Feldman et al. |
| 6,468,741 B1 | 10/2002 | Massey et al. |
| 6,472,226 B1 | 10/2002 | Barradine et al. |
| 6,479,146 B1 | 11/2002 | Caruso et al. |
| 6,509,085 B1 | 1/2003 | Kennedy |
| 6,509,196 B1 | 1/2003 | Brooks et al. |
| 6,511,814 B1 | 1/2003 | Carpenter |
| 6,524,864 B2 | 2/2003 | Decastro |
| 6,556,299 B1 | 4/2003 | Rushbrooke et al. |
| 6,566,508 B2 | 5/2003 | Bentsen et al. |
| 6,573,040 B2 | 6/2003 | Everhart et al. |
| 6,579,673 B2 | 6/2003 | McGrath et al. |
| 6,582,930 B1 | 6/2003 | Ponomarev et al. |
| 6,585,939 B1 | 7/2003 | Dapprich |
| 6,607,922 B2 | 8/2003 | LaBorde |
| 6,613,583 B1 | 9/2003 | Richter et al. |
| 6,617,488 B1 | 9/2003 | Springer et al. |
| 6,627,459 B1 | 9/2003 | Tung et al. |
| 6,653,149 B1 | 11/2003 | Tung et al. |
| 6,669,908 B2 | 12/2003 | Weyker et al. |
| 6,670,115 B1 | 12/2003 | Zhang |
| RE38,430 E | 2/2004 | Rosenstein |
| 6,720,007 B2 | 4/2004 | Walt et al. |
| 6,787,368 B1 | 9/2004 | Wong et al. |
| 6,815,218 B1 | 11/2004 | Jacobson et al. |
| 6,916,666 B1 | 7/2005 | Mendel-Hartvig et al. |
| 6,951,631 B1 | 10/2005 | Catt et al. |
| 7,044,919 B1 | 5/2006 | Catt et al. |
| 7,052,831 B2 | 5/2006 | Fletcher et al. |
| 2001/0055776 A1 | 12/2001 | Greenwalt |
| 2002/0042149 A1 | 4/2002 | Butlin et al. |
| 2002/0045273 A1 | 4/2002 | Butlin et al. |
| 2002/0070128 A1 | 6/2002 | Beckmann |
| 2002/0132282 A1 | 9/2002 | Ouyang et al. |
| 2002/0146754 A1 | 10/2002 | Kitawaki et al. |
| 2002/0164659 A1 | 11/2002 | Rao et al. |
| 2003/0017615 A1 | 1/2003 | Sidwell et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2003/0162236 A1 | 8/2003 | Harris et al. |
| 2003/0175517 A1 | 9/2003 | Voigt et al. |
| 2003/0178309 A1 | 9/2003 | Huang et al. |
| 2004/0014073 A1 | 1/2004 | Trau et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0106190 A1 | 6/2004 | Yang et al. |
| 2004/0152963 A1 | 8/2004 | March |
| 2005/0142032 A1* | 6/2005 | Hoenes et al. ............... 422/58 |
| 2005/0214827 A1* | 9/2005 | Virtanen ..................... 435/6 |
| 2006/0008921 A1* | 1/2006 | Daniels et al. ............. 436/514 |
| 2006/0175193 A1* | 8/2006 | Inganas et al. ............. 204/242 |

FOREIGN PATENT DOCUMENTS

| | | |
|---|---|---|
| EP | 0205698 A1 | 12/1986 |
| EP | 0420053 A1 | 4/1991 |
| EP | 0437287 B1 | 7/1991 |
| EP | 0469377 A2 | 2/1992 |
| EP | 0617285 A2 | 9/1994 |
| EP | 0617285 A3 | 9/1994 |
| EP | 0703454 A1 | 3/1996 |
| EP | 0462376 B1 | 7/1996 |
| EP | 0724156 A1 | 7/1996 |
| EP | 0745843 A2 | 12/1996 |
| EP | 0745843 A3 | 12/1996 |
| EP | 0859230 A1 | 8/1998 |
| EP | 0898169 B1 | 2/1999 |
| EP | 0711414 B1 | 3/1999 |
| EP | 1221616 A1 | 7/2002 |
| EP | 1255111 A1 | 11/2002 |
| GB | 2273772 A | 6/1994 |
| WO | WO 8804777 A1 | 6/1988 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |
| WO | WO 9319370 A1 | 9/1993 |
| WO | WO 9413835 A1 | 6/1994 |
| WO | WO 9415193 A1 | 7/1994 |
| WO | WO 9709620 A1 | 3/1997 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0046839 A2 | 8/2000 |
| WO | WO 0046839 A3 | 8/2000 |
| WO | WO 0047983 A1 | 8/2000 |
| WO | WO 0050891 A1 | 8/2000 |
| WO | WO 0078917 A1 | 12/2000 |
| WO | WO 0138873 A2 | 5/2001 |
| WO | WO 0163299 A1 | 8/2001 |
| WO | WO 0198765 A1 | 12/2001 |
| WO | WO 0198785 A2 | 12/2001 |
| WO | WO 01098765 A1 | 12/2001 |
| WO | WO 03005013 A1 | 1/2003 |
| WO | WO 03008971 A2 | 1/2003 |
| WO | WO 03008971 A3 | 1/2003 |
| WO | WO 2004034056 A2 | 4/2004 |
| WO | WO 2004034056 A3 | 4/2004 |

OTHER PUBLICATIONS

PCT Search Report and Written Opinion for PCT/US2004/006412, Sep. 28, 2004.
PCT Search Report and Written Opinion for PCT/US2004/006414, Sep. 28, 2004.
Abstract of DE10024145A1, Nov. 22, 2001.
Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.
PCT Search Report and Written Opinion for PCT/US2004/013180, Aug. 17, 2004.
U.S. Appl. No. 10/325,429, filed Dec. 19, 2002, Wei, et al., Self-Calibrated Flow-Through Assay Devices.
U.S. Appl. No. 10/406,577, filed Apr. 3, 2003, Yang, et al., Assay Devices That Utilize Hollow Particles.
U.S. Appl. No. 10/325,614, filed Dec. 19, 2002, Wei, et al., Reduction Of The Hook Effect In Membrane-Based Assay Devices.
U.S. Appl. No. 10/406,631, filed Apr. 3, 2003, Wei, et al., Reduction Of The Hook Effect In Assay Devices.
U.S. Appl. No. 10/718,997, filed Nov. 21, 2003, Wei, et al., Extension Of The Dynamic Detection Range Of Assay Devices.
U.S. Appl. No. 10/741,434, filed Dec. 19, 2003, Yang, et al., Laminated Assay Devices.
U.S. Appl. No. 10/742,589, filed Dec. 19, 2003, Yang, et al., Flow Control Of Electrochemical-Based Assay Devices.

U.S. Appl. No. 10/742,590, filed Dec. 19, 2003, Yang, et al., Flow-Through Assay Devices.
U.S. Appl. No. 10/718,989, filed Nov. 21, 2003, Xuedong Song, Membrane-Based Lateral Flow Assay Devices That Utilize Phosphorescent Detection.
U.S. Appl. No. 10/718,996, filed Nov. 21, 2003, Ning Wei, Method Of Reducing The Sensitivity Of Assay Devices.
U.S. Appl. No. 10/836,093, filed Apr. 30, 2004, David S. Cohen, Optical Detection Systems.
U.S. Appl. No. 10/790,617, filed Mar. 1, 2004, Boga, et al., Assay Devices Utilizing Chemichronic Dyes.
Abstract of Japanese Patent No. JP 8062214, Mar. 8, 1996.
Abstract of Article—*Factors influencing the formation of hollow ceramic microspheres by water extraction of colloidal droplets*, J. Mater. Res., vol. 10, No. 1, p. 84, 1996.
Article—*A conductometric biosensor for biosecurity*, Zarini Muhammid-Tahir and Evangelyn C. Alocilja, Biosensors and Bioelectronics 18, 2003, pp. 813-819.
Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*A Thermostable Hydrogen Peroxide Sensor Based on "Wiring" of Soybean Peroxidase*, Mark S. Vreeke, Iain Tsun Yong, and Adam Heller, Analytical Chemistry, vol. 67, No. 23, Dec. 1, 1995, pp. 4247-4249.
Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Analysis of electrical equivalent circuit of quartz crystal resonator loaded with viscous conductive liquids*, Journal of Electroanalytical Chemistry, vol. 379, 1994, pp. 21-33.
Article—*Application of rod-like polymers with ionophores as Langmuir-Blodgett membranes for Si-based ion sensors*, Sensors and Actuators B, 1992, pp. 211-216.
Article—*Attempts to Mimic Docking Processes of the Immune System: Recognition of Protein Multilayers*, W . Muller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.
Article—*Biochemical Diagnosis of Vaginitis: Determination of Diamines in Vaginal Fluid*, Kirk C.S. Chen, Richard Amsel, DavidAa. Eschenbach, and King K. Holmes, The Journal of Infectious Diseases, vol. 145, No. 3, Mar. 1982, pp. 337-345.
Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.
Article—*Direct Observation of Streptavidin Specifically Adsorbed on Biotin-Functionalized Self-Assembled Monolayers with the Scanning Tunneling Microscope*, Lukas Häuussling, Bruno Michel, Helmut Ringsdorf, and Heinrich Rohrer, Angew Chem. Int. Ed. Engl., vol. 30, No. 5, 1991, pp. 569-572.
Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.
Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages, 1995.
Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.
Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.
Article—*Fine Structure of Human Immunodeficiency Virus (HIV) and Immunolocalization of Structural Proteins*, Hans R. Gelderblom, Elda H.S. Hausmann, Muhsin Ozel, George Pauli, and Meinrad A. Koch, Virology, vol. 156, No. 1, Jan. 1987, pp. 171-176.
Article—Flow-*Based Microimmunoassay*, Analytical Chemistry, vol. 73, No. 24, Mark A. Hayes, Nolan A. Poison, Allison, N. Phayre, and Antonia A. Garcia, Dec. 15, 2001, pp. 5896-5902.
Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.
Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.
Article—*Hollow latex particles: synthesis and applications*, Charles J. McDonald and Michael J. Devon, Advances in Colloid and Interface Science, Vo. 99, 2002, pp. 181-213.
Article—*How to Build a Spectrofluorometer*, Spex Fluorolog 3, Horiba Group, pp. 1-14, 2004.
Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.
Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phosphorescent Nanospheres as Markers for Optical Assays*, Jens M. Kilmer, Ingo Klimant, Christian Krause, Harald Preu, Werner Kunz, and Otto S. Wolfbeis, Bioconjugate Chem., vol. 12, No. 6, 2001, pp. 883-889.
Article—*Intelligent Gels*, Yoshihito Osada and Simon B. Ross-Murphy, Scientific American, May 1993, pp. 82-87.
Article—*Latex Immunoassays*, Leigh B. Bangs, Journal of Clinical Immunoassay, vol. 13, No. 3, 1990, pp. 127-131.
Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.
Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.
Article—*Microfabrication by Microcontact Printing of Self-Assembled Monolyaers*, James L. Wilbur, Armit Kumar, Enoch Kim, and George M. Whitesides, Advanced Materials, vol. 6, No. 7/8, 1994, pp. 600-604.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.

Article—*Molecular Design Temperature- Responsive Polymers as Intelligent Materials*, Teruo Okano, Advances in Polymer Science, pp. 179-197, (received Jul. 1992).

Article—*Molecular Gradients of wSubstituted Alkanethiols on Gold: Preparation and Characterization*, Bo Liedberg and Pentti Tengvall, Langmuir, vol. 11, No. 10, 1995, pp. 3821-3827.

Article—*Monofunctional Derivatives of Coproporphyrins for Phosphorescent Labeling of Proteins and Binding Assays*, Tomas C. O'Riordan, Aleksi E. Soini, and Dmitri B. Papkovsky, Analytical Biochemistry, vol. 290, 2001, pp. 366-375.

Article—*Nanostructuredrm Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp. 352-357, May 1997.

Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.

Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem Soc., vol. 119, No. 13, 1997, pp. 3017-3026.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives of $(n^5-C_5H_5)Mn(CO)_3$*, Doris Kang and Mark S. Wrighton, Langmuir, vol. 7, No. 10, 1991, pp. 2169-2174.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.

Article—*Photolithography of self-assembled monolayers: optimization of protecting groups by an electroanalytical method*, Jamila Jermane, Tanya Boutrous, and Richard Giasson, Can. J. Chem., vol. 74, 1996, pp. 2509-2517.

Article—*Photopatterning and Selective Electroless Metallization of Surface—Attached Ligands*, Walter J. Dressick, Charles S. Dulcey, Jacque H. Georger, Jr., and Jeffrey M. Calvert, American Chemical Society, 2 pages, 1993.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Principle and Applications of Size-Exclusion Chromatography*, Impact Analytical, pp. 1-3, 2004.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Quantitative Prediction of Surface Segregation*, M. P. Seah, Journal of Catalysts, vol. 57, 1979, pp. 450-457.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Responsive Gels: vol. Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages, 1993.

Article—*Room-Temperature Phosphorescent Palladium-Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films for Nanofabrication*, Elizabeth a. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Separation-Free Sandwich Enzyme Immunoassays Using Microporous Gold Electrodes and Self-Assembled Monolayer/Immobolized Capture Antibodies*, Chuanming Duan and Mark E. Meyerhoff, Analytical Chemistry, vol. 66, No. 9, May 1, 1994, pp. 1369-1377.

Article—*Stimuli-Responsive Poly(N-isopropylacrylamide) Photo- and Chemical-Induced Phase Transitions*, Advances in Polymer Science, pp. 50-65, (received Jul. 1992).

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article—*The Use of Self-Assembled Monolayers and a Selective Etch to Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Volume Phase Transition of N-Alkylacrylamide Gels*, S. Saito, M. Konno, and H. Inomata, Advances in Polymer Science, vol. 109, 1992, pp. 207-232.

Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.

8 Photographs of Accu-chek® Blood Glucose Meter, (2004).

*AMI Screen Printers—Product Information*, 4 pages, (2004).

CELQUAT® SC-230M (28-6830), CELQUAT® SC-240C and SC-230M, from National Starch & Chemical, 1 page, (Feb. 72000).

CELQUAT® SC-230M (28-6830), Polyquaternium-10, from National Starch & Chemical, 1 page, (2001).

*Dualite® Polymeric Microspheres*, from Pierce & Stevens Corp. a subsidiary of Sovereign Specialty Chemicals, Inc., 2 pages, (2001).

*Dynabeads® Biomagnetic Separation Technology—The Principle from Dynal Biotech*, 2 pages, (2004).
*ECCOSPHERES® glass microspheres—hollow glass microspheres* from Emerson & Cuming Composite Materials, Inc., 1 page, (2004).
*Fluorescent Microsphere Standards for Flow Cytometry and Fluorescence Microscopy* from Molecular Probes, pp. 1-8, (2000).
*FluoSpheres® Fluorescent Microspheres*, Product Information from Molecular Probes, Mar. 13, 2001, pp. 1-6.
*Magnetic Microparticles*, Polysciences, Inc. Technical Data Sheet 438, 2 pages, (2004).
*Making sun exposure safer for everyone* from Rohm and Haas Company (Bristol Complex), 2 pages, (2004).
Pamphlet—The ClearPlan® Easy Fertility Monitor, (Jul. 12, 2002).
*POSS Polymer Systems* from Hybrid Plastics, 3 pages, (2000).
*The colloidal state*, Introduction to Colloid and Surface Chemistry, $4^{th}$ Ed., 17 pages, (1992).
*Working With FluoSpheres® Fluorescent Microspheres*, Properties and Modifications, Product Information from Molecular Probes, Mar. 9, 2001, pp. 1-5.
PCT Search Report for PCT/US03/21520, Dec. 15, 2003.
PCT Search Report for PCT/US02/37653, Apr. 7, 2004.
PCT Search Report for PCT/US03/28628, Mar. 18, 2004.
PCT Search Report for PCT/US03/34543, Apr. 6, 2004.
PCT Search Report for PCT/US03/34544, Apr. 20, 2004.

* cited by examiner

METHOD FOR EXTENDING THE DYNAMIC DETECTION RANGE OF ASSAY DEVICES

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assays typically involve mixing the test sample with detectable probes, such as dyed latex or a radioisotope, which are conjugated with a specific binding member for the analyte. The conjugated probes form complexes with the analyte. These complexes then reach a zone of immobilized antibodies where binding occurs between the antibodies and the analyte to form ternary "sandwich complexes." The sandwich complexes are localized at the zone for detection of the analyte. This technique may be used to obtain quantitative or semi-quantitative results. Some examples of such sandwich-type assays are described in. by U.S. Pat. No. 4,168,146 to Grubb, et al. and U.S. Pat. No. 4,366,241 to Tom, et al. An alternative technique is the "competitive-type" assay. In a "competitive-type" assay, the label is typically a labeled analyte or analyte-analogue that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

Despite the benefits achieved from these devices, many conventional lateral flow assays encounter significant inaccuracies when exposed to relatively high analyte concentrations. For example, assays that rely on optical detection (e.g., fluorescence, reflectance, phosphorescence, etc.) often become inaccurate at high analyte concentrations. Specifically, the probes are usually not only captured on the surface of the membrane device, but also within the interior of the assay device. Unfortunately, most optical detection techniques are not capable of detecting those probes captured deep within the interior of the assay device. In addition, fluorescent probes sometimes exhibit "self-quenching" when placed too close together. Self-quenching is a well-known phenomenon that occurs when two or more fluorescent materials interact photochemically to quench each other's fluorescence. Thus, fluorescent probes may begin to exhibit self-quenching at high analyte concentrations, which actually results in a decrease in the fluorescent intensity. Those problems often limit the detection range and result in an inaccurate detection of an analyte.

In response to these or other problems, several assays configurations have been proposed. For example, EP 0462376 to Ching describes an assay device that includes a solid phase having at least two defined and marked detection sites in sequential fluid-flow contact. The first detection site is a capture site immobilized with a capture reagent capable of competing with the analyte for binding to a conjugate. A second detection site is a conjugate recovery site that includes a conjugate recovery agent different from the capture reagent for binding to the conjugate or a complex thereof that passes through the capture site. As the amount of analyte in the test sample increases, the more the bonding sites of the conjugate are occupied by analyte molecules and the less the conjugate is free to bind to the capture reagent. Instead, the analyte/conjugate complexes pass through the capture site and migrate into the conjugate recovery site. A comparative analysis of the amounts of label at each site indicates the amount of analyte in the test sample.

Nevertheless, a need still exists for a method of extending the dynamic detection range of an assay device in an accurate, yet simple and cost-effective manner.

SUMMARY OF THE INVENTION

In accordance with one embodiment of the present invention, a flow-through assay device for detecting the presence or quantity of an analyte residing in a test sample is disclosed. The flow-through assay device comprises a porous membrane that is in communication with detection probes and calibration probes, the detection probes being conjugated with a specific binding member for the analyte. If desired, the conjugated detection probes may comprise a substance selected from the group consisting of chromogens, catalysts, luminescent compounds (e.g., fluorescent, phosphorescent, etc.), radioactive compounds, visual labels, liposomes, and combinations thereof. The specific binding member may be selected from the group consisting of antigens, haptens, aptamers, primary or secondary antibodies, biotin, and combinations thereof.

The porous membrane defines a detection zone within which a first capture reagent is immobilized that is configured to bind to at least a portion of the conjugated detection probes or complexes thereof to generate a detection signal having an intensity. In one embodiment, the first capture reagent is selected from the group consisting of antigens, haptens, protein A or G, neutravidin, avidin, streptavidin, captavidin, primary or secondary antibodies, and complexes thereof. For instance, the first capture reagent may bind to complexes formed between the analyte and the conjugated detection probes.

To further extend the dynamic detection range of the assay device, the porous membrane also defines a compensation zone located downstream from the detection zone. A second capture reagent is immobilized within the compensation zone that is configured to bind to the conjugated detection probes or complexes thereof passing through the detection zone to generate a compensation signal having an intensity. In one embodiment, the second capture reagent is selected from the group consisting of antigens, haptens, protein A or G, neutravidin, avidin, streptavidin, captavidin, primary or secondary antibodies, and complexes thereof. In another embodiment, the second capture reagent comprises a polyelectrolyte. The polyelectrolyte may be positively charged, negatively charged, amphiphilic, etc. Regardless of the material selected for the second capture reagent, the intensity of the compensation signal is inversely proportional to the intensity of the detection signal. Accordingly, the ratio of the detection signal intensity to the compensation signal intensity is proportional to analyte concentration, and thus may be used for determining the amount of the analyte in the test sample.

The accuracy of the detection and compensation signals under actual test conditions may be further improved using self-calibration techniques. Specifically, the porous membrane is also in communication with calibration probes and comprises a calibration zone within which a third capture reagent is immobilized that is configured to bind to the calibration probes to generate a calibration signal having an intensity. The calibration signal is substantially constant in intensity relative to the intensities of the detection and compensation signals. Thus, the calibration signal may be used to calibrate the detection and compensation signals.

In accordance with another embodiment of the present invention, a method for detecting the presence or quantity of an analyte residing in a test sample is disclosed. The method comprises:

i) providing a flow-through assay device comprising a porous membrane, the porous membrane being in communication with detection probes and calibration probes, the detection probes being conjugated with a specific binding member for the analyte, the porous membrane defining a detection zone within which a first capture reagent is immobilized, a compensation zone within which a second capture reagent is immobilized, and a calibration zone within which a third capture reagent is immobilized, wherein the compensation zone is located downstream from the detection zone;

ii) contacting a test sample containing the analyte with the conjugated detection probes and the calibration probes;

iii) measuring a detection signal intensity generated at the detection zone, a compensation signal intensity generated at the compensation zone, and a calibration signal intensity generated at the calibration zone;

iv) comparing the intensity of the detection signal to the compensation signal, wherein the intensity of the compensation signal is inversely proportional to the intensity of the detection signal; and v) calibrating the compared intensities of the detection signal and the compensation signal with the intensity of the calibration signal, wherein the intensity of the calibration signal is substantially constant relative to the intensities of the detection signal and the calibration signal. If desired, the method may further comprise generating a calibration curve by plotting the ratio of the detection signal intensity to the compensation signal intensity calibrated by the intensity of the calibration signal for a plurality of predetermined analyte concentrations.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
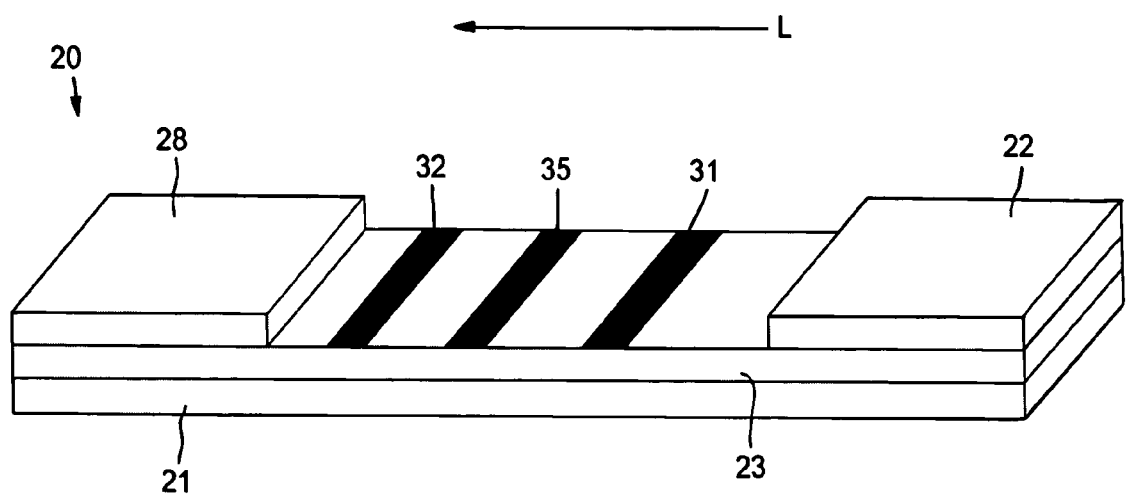
FIG. 1 is a perspective view of one embodiment of a flow-through assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyphene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample may, for instance, include materials obtained directly from a source, as well as materials pretreated using techniques, such as, but not limited to, filtration, precipitation, dilution, distillation, mixing, concentration, inactivation of interfering components, the addition of reagents, and so forth. The test sample may be derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. Besides physiological fluids, other liquid samples may be used, such as water, food products, and so forth. In addition, a solid material suspected of containing the analyte may also be used as the test sample.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a flow-through assay device for detecting the presence or quantity of an analyte residing in a test sample. The device utilizes a detection zone and compensation zone within which are immobilized capture reagents. The present inventor has discovered that the presence of a compensation zone may enable the detection of an analyte over extended concentration ranges. In particular, the signal from the compensation zone may compensate for the lost signal resulting from those probes that are embedded too deep within the interior of the assay device and/or those probes that exhibit self-quenching.

Referring to FIG. 1, for instance, one embodiment of a sandwich-type, flow-through assay device 20 that may be formed according to the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad (not shown) that is in fluid communication with the porous membrane 23. Some suitable materials that may be used to form the sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

In the illustrated embodiment, the test sample travels from the sample pad (not shown) to a conjugate pad 22 that is placed in communication with one end of the sample pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, a predetermined amount of detection probes are applied at various locations of the device 20. Any substance generally capable of generating a signal that is detectable visually or by an instrumental device may be used as detection probes. Various suitable substances may include chromogens; catalysts; luminescent compounds (e.g., fluorescent, phosphorescent, etc.); radioactive compounds; visual labels, including colloidal metallic (e.g., gold) and non-metallic particles, dye particles, enzymes or substrates, or organic polymer latex particles; liposomes or other vesicles containing signal producing substances; and so forth. For instance, some enzymes suitable for use as detection probes are disclosed in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable detection probes may be described in U.S. Pat. No. 5,670,381 to Jou, et al. and U.S. Pat. No. 5,252,459 to Tarcha, et al., which are incorporated herein in their entirety by reference thereto for all purposes.

In some embodiments, the detection probes may contain a fluorescent compound that produces a detectable signal. The fluorescent compound may be a fluorescent molecule, polymer, dendrimer, particle, and so forth. Some examples of suitable fluorescent molecules, for instance, include, but are not limited to, fluorescein, europium chelates, phycobiliprotein, rhodamine and their derivatives and analogs.

The detection probes, such as described above, may be used alone or in conjunction with a microparticle (sometimes referred to as "beads" or "microbeads"). For instance, naturally occurring microparticles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic microparticles may also be utilized. For example, in one embodiment, latex microparticles that are labeled with a fluorescent or colored dye are utilized. Although any latex microparticle may be used in the present invention, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable microparticles may be described in U.S. Pat. No. 5,670,381 to Jou, et al. and U.S. Pat. No. 5,252,459 to Tarcha, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In some instances, it is desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Figure 2:
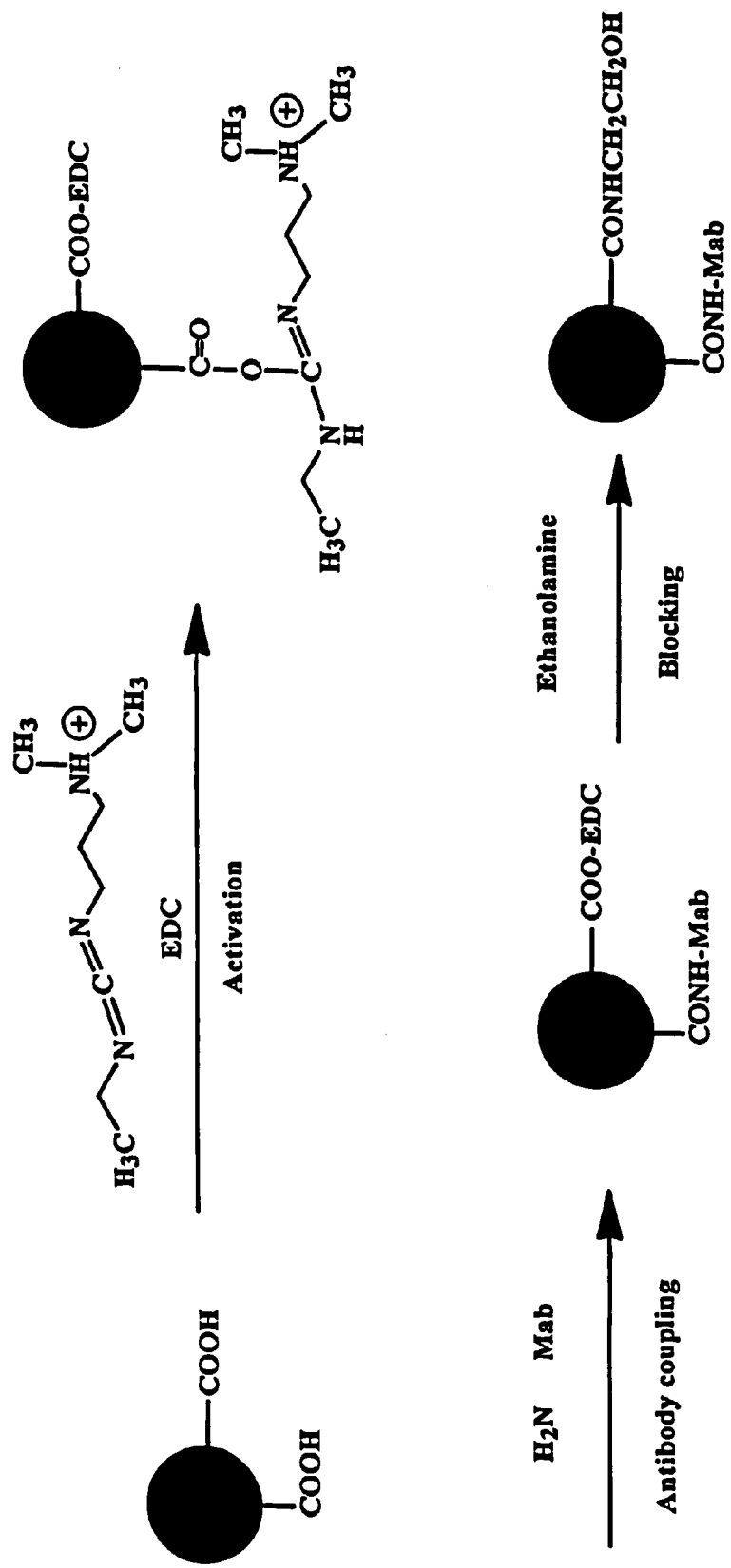
FIG. 2 is a graphical illustration of one embodiment for covalently conjugating an antibody to a detection probe.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the microparticles are capable of direct covalent linking with a protein without the need for further modification. For example, referring to FIG. 2, one embodiment of the present invention for covalently conjugating a particle-containing detection probe is illustrated. As shown, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino)ethane sulfonic acid (MES) (e.g., pH of 5.3). As shown, the resulting detection probes may then be blocked with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to FIG. 1, the assay device 20 may also contain a detection zone 31 within which is immobilized a first capture reagent that is capable of binding to the conjugated detection probes. For example, in some embodiments, the first capture reagent may be a biological capture reagent. Such biological capture reagents are well known in the art and may include, but are not limited to, antigens, haptens, protein A or G, neutravidin, avidin, streptavidin, captavidin, primary or secondary antibodies (e.g., polyclonal, monoclonal, etc.), and complexes thereof. In many cases, it is desired that these biological capture reagents are capable of binding to a specific binding member (e.g., antibody) present on the detection probes. The first capture reagent serves as a stationary binding site for complexes formed between the analyte and conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized capture reagent. Upon being bound to the immobilized capture reagent, the complexed probes form a new ternary sandwich complex.

The detection zone 31 may generally provide any number of distinct detection regions so that a user may better determine the concentration of a particular analyte within a test sample. Each region may contain the same capture reagents, or may contain different capture reagents for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

Referring again to FIG. 1, the porous membrane 23 also contains a compensation zone 35 positioned downstream from the detection zone 31. The compensation zone 35 generally provides a single distinct region (e.g., line, dot, etc.), although multiple regions are certainly contemplated by the present invention. For instance, in the illustrated embodiment, a single line is utilized. The compensation zone 35 may be disposed in a direction that is substantially perpendicular to the flow of the test sample through the device 20. Likewise, in some embodiments, the zone 35 may be disposed in a direction that is substantially parallel to the flow of the test sample through the device 20.

Regardless of its configuration, a second capture reagent is immobilized on the membrane 35 within the compensation zone 35. The second capture reagent serves as a stationary binding site for any conjugated detection probes and/or analyte/conjugated probe complexes that do not bind to the first capture reagent at the detection zone 31. Because it is desired that the second capture reagent bind to both complexed and uncomplexed conjugated detection probes, the second capture reagent is normally different than the first capture reagent. In one embodiment, the second capture reagent is a biological capture reagent (e.g., antigens, haptens, protein A or G, neutravidin, avidin, streptavidin, primary or secondary antibodies (e.g., polyclonal, monoclonal, etc.), and complexes thereof) that is different than the first capture reagent. For example, the first capture reagent may be a monoclonal antibody (e.g., CRP Mab1), while the second capture reagent may be avidin (a highly cationic 66,000-dalton glycoprotein), streptavidin (a nonglycosylated 52,800-dalton protein), neutravidin (a deglysolated avidin derivative), and/or captavidin (a nitrated avidin derivative). In this embodiment, the second capture reagent may bind to biotin, which is biotinylated or contained on detection probes conjugated with a monoclonal antibody different than the monoclonal antibody of the first capture reagent (e.g., CRP Mab2).

In addition, it may also be desired to utilize various non-biological materials for the second capture reagent of the compensation zone 35. In many instances, such non-biological capture reagents may be particularly desired to better ensure that all of the remaining conjugated detection probes and/or analyte/conjugated probe complexes are immobilized at the compensation zone 35. For instance, in some embodiments, the second capture reagent may include a polyelectrolyte.

The polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the porous membrane, and so forth. In particular, the distributed charge of a polyelectrolyte allows it to bind to substances having an opposite charge. Thus, for example, polyelectrolytes having a net positive charge are often better equipped to bind with detection probes that are negatively charged, while polyelectrolytes that have a net negative charge are often better equipped to bind to detection probes that are positively charged. Thus, in such instances, the ionic interaction between these molecules allows the required binding to occur within the compensation zone 35. Nevertheless, although ionic interaction is primarily utilized to achieve the desired binding in the compensation zone 35, it has also been discovered that polyelectrolytes may bind with detection probes having a similar charge.

Because the polyelectrolyte is designed to bind to detection probes, it is typically desired that the polyelectrolyte be substantially non-diffusively immobilized on the surface of the porous membrane 23. Otherwise, the detection probes would not be readily detectable by a user. Thus, the polyelectrolytes may be applied to the porous membrane 23 in such a manner that they do not substantially diffuse into the matrix of the porous membrane 23. In particular, the polyelectrolytes typically form an ionic and/or covalent bond with functional groups present on the surface of the porous membrane 23 so that they remain immobilized thereon. Although not required, the formation of covalent bonds between the polyelectrolyte and the porous membrane 23 may be desired to more permanently immobilize the polyelectrolyte thereon.

For example, in one embodiment, the monomers used to form the polyelectrolyte are first formed into a solution and then applied directly to the porous membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the porous membrane 23, thereby immobilizing the resulting polyelectrolyte thereon. For example, in one embodiment, an ethyleneimine monomer may form a covalent bond with a carboxyl group present on the surface of some porous membranes (e.g., nitrocellulose).

In another embodiment, the polyelectrolyte may be formed prior to application to the porous membrane 23. If desired, the polyelectrolyte may first be formed into a solution using organic solvents, water, and so forth. Thereafter, the polyelectrolytic solution is applied directly to the porous membrane 23 and then dried. Upon drying, the polyelectrolyte may form an ionic bond with certain functional groups present on the surface of the porous membrane 23 that have a charge opposite to the polyelectrolyte. For example, in one embodiment, positively-charged polyethyleneimine may form an ionic bond with negatively-charged carboxyl groups present on the surface of some porous membranes (e.g., nitrocellulose).

In addition, the polyelectrolyte may also be crosslinked to the porous membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. No. 3,700,623 to Keim and U.S. Pat. No. 3,772,076 to Keim, U.S. Pat. No. 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/or polyamidoamine compounds that contain epoxide rings and quaternary ammonium groups that may form covalent bonds with carboxyl groups present on certain types of porous membranes (e.g., nitrocellulose) and crosslink with the polymer backbone of the porous membrane when cured.

In some embodiments, the crosslinking temperature may range from about 50° C. to about 120° C. and the crosslinking time may range from about 10 to about 600 seconds.

Although various techniques for non-diffusively immobilizing polyelectrolytes on the porous membrane 23 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the porous membrane 23.

Figure 3:
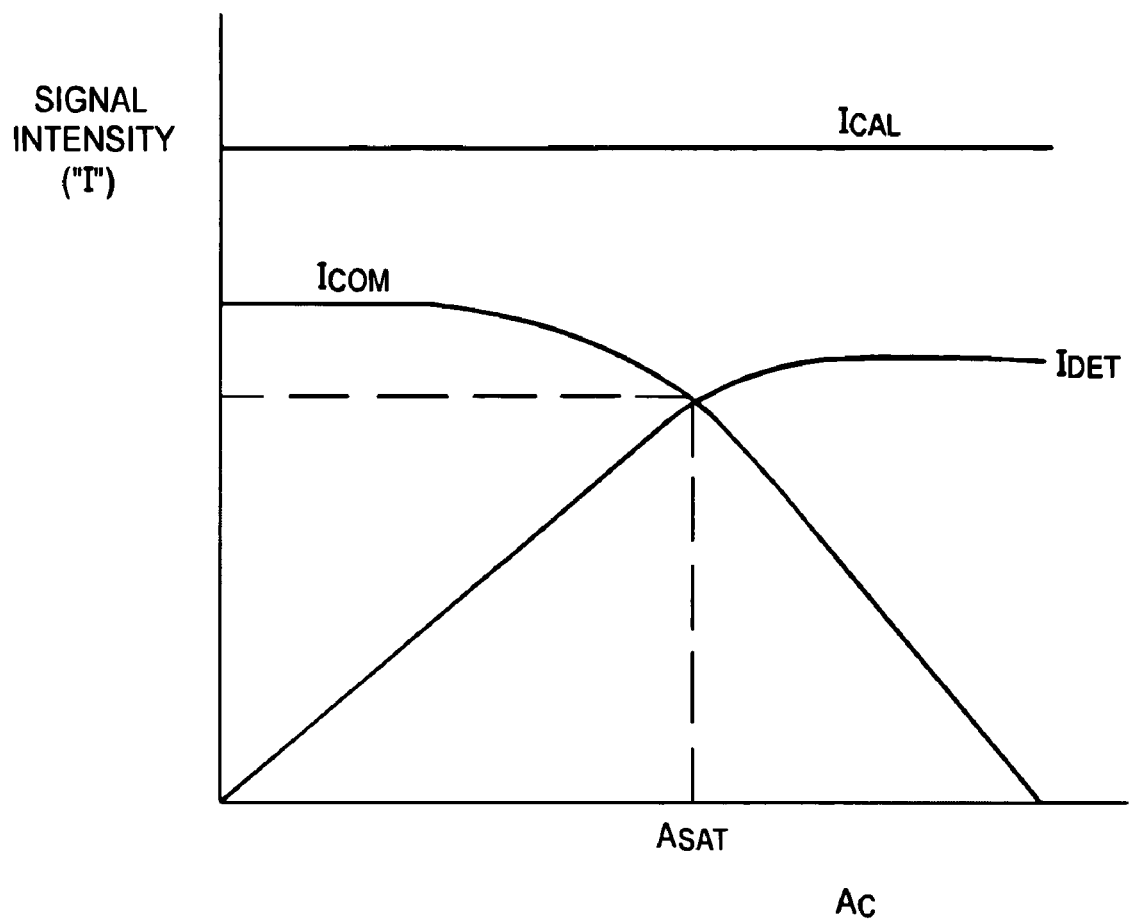
FIG. 3 is graphical illustration of the relationship between analyte concentration and signal intensities for the detection and compensation zones in accordance with one embodiment of the present invention.

Regardless of the material from which the second capture reagent is formed, the compensation zone 35 may improve the analyte detection range of the assay device 20. This phenomenon is illustrated graphically in FIG. 3. As shown, the intensity of the signal at the detection zone 31 ("$I_{det}$") initially increases as more of the analyte is captured at the detection zone 31. Ideally, the measured detection signal intensity would continue to increase linearly for higher analyte concentrations. However, optical detection methods (e.g., fluorescence and reflectance) do always not provide such an ideal measurement, particularly at relatively high detection probe concentrations. Specifically, at some point, the detection zone 31 would be unable to signal the further accumulation of detection probes. As a result, the signal at the detection zone 31 would level off or even decrease. For instance, as shown in FIG. 3, $I_{det}$ may begin to level off at an analyte concentration of "$A_{sat}$" as the analyte concentration further increases.

In accordance with the present invention, however, the intensity signal at the compensation zone ("$I_{com}$") may be measured to account for the inability of the detection zone 31 to respond to higher analyte concentrations. When no analyte is present, $I_{com}$ will be at its maximum intensity because all of the conjugated detection probes will bind to the compensation zone 35. As the analyte concentration is increased, $I_{com}$ likewise decreases due to the retention of a greater number of analyte/conjugated probe complexes by the detection zone 31. As a result of the inversely proportional relationship between the detection and compensation zone signal intensities described above, the present inventor has discovered that the concentration of an analyte may be more effectively measured over an extended range by comparing the signal intensity at both the detection and compensation zones. Specifically, the total amount of detection probes is predetermined (e.g., empirically). Because a predetermined amount of detection probes are present, the amount of detection probes captured at the compensation zone 35 is inversely proportional to the amount of detection probes at the detection zone 31. Thus, the amount of detection probes captured at the compensation zone 35 may be measured relatively accurately, even when large amounts of detection probes are captured at the detection zone 31 and the amount of such amount of such detection probes cannot be measured accurately. For example, in one embodiment, the amount of analyte is directly proportional to the ratio of $I_{det}$ to $I_{com}$. Based upon the intensity range in which the detection and compensation zones fall, the general concentration range for the analyte may be determined. If desired, the ratio of $I_{det}$ to $I_{com}$ may be plotted versus the analyte concentration for a range of known analyte concentrations to generate an intensity curve. To determine the quantity of analyte in an unknown test sample, the signal ratio may then be converted to analyte concentration according to the intensity curve. It should be noted that the capturing efficiency of the complexed and uncomplexed conjugated detection probes is generally the same for any given sample. Accordingly, the variation in capturing efficiency is not believed to significantly interfere with the results from sample-to-sample because the ratio of intensities (i.e., $I_{det}/I_{com}$) is used instead of absolute signal intensity. It should also be noted that alternative mathematical relationships between $I_{det}$ and $I_{com}$ may be plotted versus the analyte concentration to generate the calibration curve. For example, in one embodiment, the value of $I_{det}/(I_{det}+I_{com})$ may be plotted versus analyte concentration to generate the intensity curve.

Although the detection zone 31 and compensation zone 35 may indicate the presence of an analyte, it is often difficult to accurately determine the relative concentration of the analyte within the test sample under actual test conditions. Thus, the assay device 20 may also include a calibration zone 32. In this embodiment, the calibration zone 32 is formed on the porous membrane 23 and is positioned downstream from the detection zone 31 and compensation zone 35. Alternatively, however, the calibration zone 32 may also be positioned upstream from the detection zone 31 and/or compensation zone 35.

The calibration zone 32 is provided with a third capture reagent that is capable of binding to calibration probes that pass through the length of the membrane 23. The calibration probes may be formed from the same or different materials as the detection probes, and may be conjugated with a specific binding member as described above. Generally speaking, the calibration probes are selected in such a manner that they do not bind to the first or second capture reagent at the detection zone 31 and compensation zone 35. The third capture reagent may also be the same or different than the capture reagents used in the detection zone 31 or compensation zone 35. For example, in one embodiment, the third capture reagent is a biological capture reagent, such as antigens, haptens, protein A or G, neutravidin, avidin, streptavidin, captavidin, primary or secondary antibodies, or complexes thereof. Moreover, similar to the detection zone 31 and compensation zone 35, the calibration zone 32 may also provide any number of distinct calibration regions in any direction so that a user may better determine the concentration of a particular analyte within a test sample.

The calibration zone 32 may improve the accuracy of the detected analyte. The calibration zone 32 may also eliminate requirement of separate calibration for measurements carried out at a different time under different conditions. The total amount of the calibration probes and the total amount of the third capture reagent on the calibration zone 32 is predetermined. Thus, the amount of the captured calibration probes and the resulting calibration signal ideally fluctuates in a manner similar to what would occur at the detection zone 31 based on changing assay conditions, e.g., temperature fluctuation. Desirably, the third capture reagent has a similar degradation profile to that of the first capture reagent at the detection zone 31. The calibration probes may also have a similar degradation profile to that of the detection probes. The signal fluctuation of both the detection probes and the calibration probes is ideally the same or similar with changed conditions.

Thus, the calibration zone 32 may be used to calibrate the intensities of the detection zone 31 and compensation zone 35 under different assay conditions. For example, referring again to FIG. 3, the amount of analyte may be directly proportional to the ratio of $I_{det}$ to the product of the calibration intensity ("$I_{cal}$") and $I_{com}$ (i.e., $I_{det}/(I_{cal})(I_{com})$). If desired, this may be plotted versus the analyte concentration for a range of known analyte concentrations to generate a calibration curve. To determine the quantity of analyte in an unknown test sample, the signal ratio may then be converted to analyte concentration according to the calibration curve. It should also be noted that alternative mathematical relationships may be plotted versus the analyte concentration to generate the calibration curve.

Figure 4:
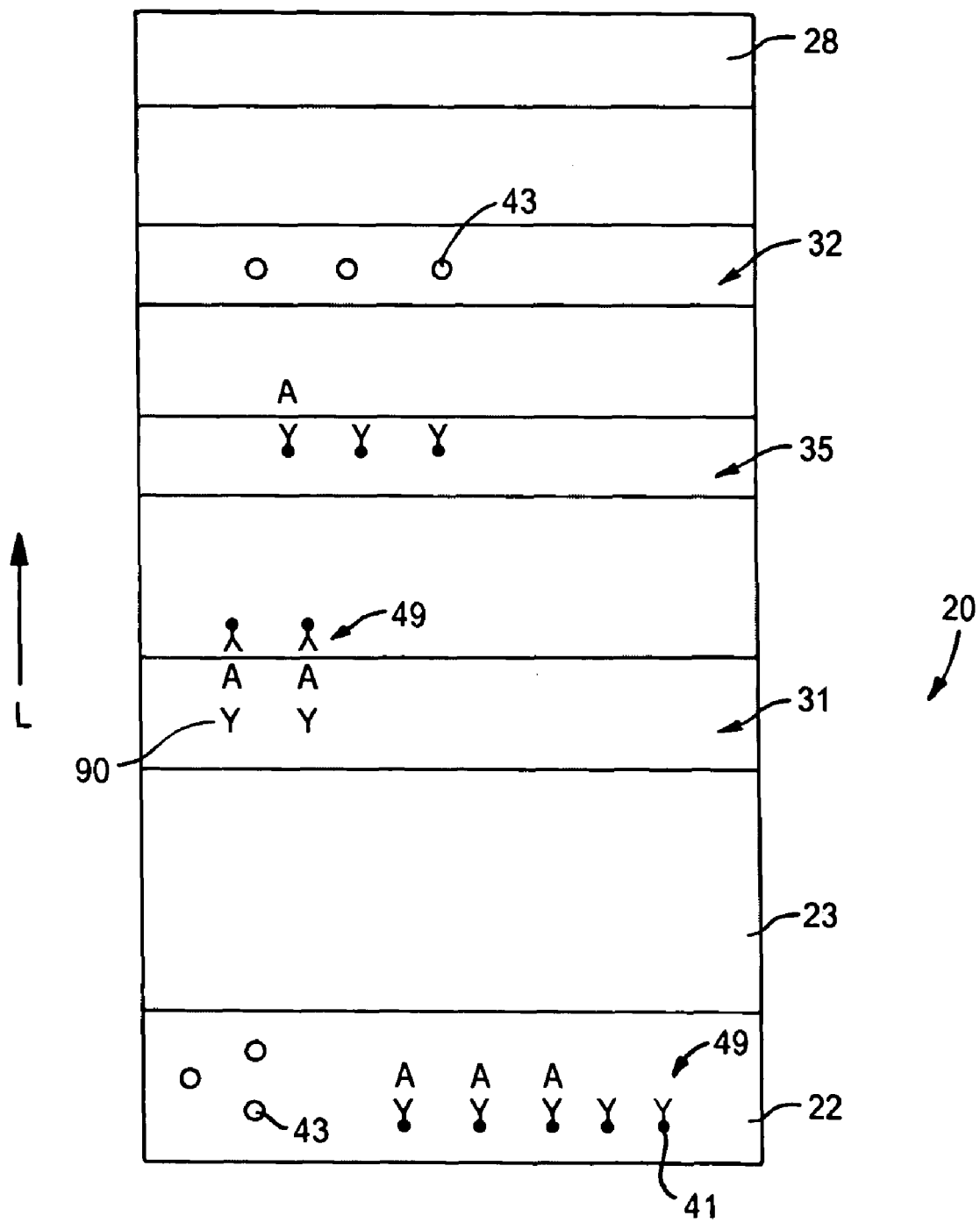
FIG. 4 is a graphical illustration of the mechanism used for one embodiment of a sandwich assay format of the present invention.

Referring to FIG. 4, one embodiment of a method for detecting the presence of an analyte utilizing fluorescent probes will now be described in more detail. Initially, a test sample containing an analyte A is applied to the sample pad. From the sample pad, the test sample travels in the direction "L" to the conjugate pad 22, where the analyte A mixes with conjugated fluorescent detection probes 41 and fluorescent calibration probes 43 (may or may not be conjugated). Although the use of fluorescence is utilized in this particular embodiment, it should be understood that other optical detection techniques, such as phosphorescence, reflectance, etc., are equally suitable for use in the present invention. For example, in one embodiment, as is well known in the art, a reflectance spectrophotometer or reader may be utilized to detect the presence of probes that exhibit a visual color (e.g. dyed latex microparticles). One suitable reflectance reader is described, for instance, in U.S. patent application Pub. No. 2003/0119202 to Kaylor, et al., which is incorporated herein in its entirety by reference thereto for all purposes.

Nevertheless, in the embodiment illustrated in FIG. 4, the analyte A binds with the conjugated fluorescent detection probes 41 to form analyte/conjugated probe complexes 49. At the detection zone 31, these complexes 49 are captured by a first capture reagent 90. Any uncomplexed conjugated fluorescent detection probes 41 and/or unbound analyte/conjugated probe complexes 49 then travel to the compensation zone 35 where they bind to a second capture reagent (not shown). Finally, the fluorescent calibration probes 43 travel through both the detection zone 31 and compensation zone 35 to bind with a third capture reagent (not shown) at the calibration zone 32.

Once captured, the fluorescence signal of the probes at the detection zone 31, compensation zone 35, and calibration zone 32 may be measured using fluorescence detection. Fluorescence is the result of a three-stage process that occurs in certain fluorescent compounds. In the first stage, energy is supplied by an external source, such as an incandescent lamp or a laser and absorbed by the fluorescent compound, creating an excited electronic singlet state. In the second stage, the excited state exists for a finite time during which the fluorescent compound undergoes conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorescent compound to its ground state. The emitted energy is lower than its excitation energy (light or laser) and thus of a longer wavelength. This shift or difference in energy or wavelength allows the emission energy to be detected and isolated from the excitation energy.

Fluorescence detection generally utilizes wavelength filtering to isolate the emission photons from the excitation photons, and a detector that registers emission photons and produces a recordable output, usually as an electrical signal or a photographic image. There are generally four recognized types of detectors: spectrofluorometers and microplate readers; fluorescence microscopes; fluorescence scanners; and flow cytometers. One suitable fluorescence detector for use with the present invention is a FluoroLog III Spectrofluorometer, which is sold by SPEX Industries, Inc. of Edison, N.J.

If desired, a technique known as "time-resolved fluorescence detection" may also be utilized in the present invention. Time-resolved fluorescence detection is designed to reduce background signals from the emission source or from scattering processes (resulting from scattering of the excitation radiation) by taking advantage of the fluorescence characteristics of certain fluorescent materials, such as lanthanide chelates of europium (Eu (III)) and terbium (Tb (III)). Such chelates may exhibit strongly red-shifted, narrow-band, long-lived emission after excitation of the chelate at substantially shorter wavelengths. Typically, the chelate possesses a strong ultraviolet absorption band due to a chromophore located close to the lanthanide in the molecule. Subsequent to light absorption by the chromophore, the excitation energy may be transferred from the excited chromophore to the lanthanide. This is followed by a fluorescence emission characteristic of the lanthanide. The use of pulsed excitation and time-gated detection, combined with narrow-band emission filters, allows for specific detection of the fluorescence from the lanthanide chelate only, rejecting emission from other species present in the sample that are typically shorter-lived or have shorter wavelength emission. Other time-resolved techniques for measuring fluorescence are described in U.S. Pat. No. 5,585,279 to Davidson and U.S. Pat. No. 5,637,509 to Hemmila, et al., which are incorporated herein in their entirety by reference thereto for all purposes.

Regardless of the technique used to measure fluorescence, the absolute amount of the analyte may be ascertained by comparing the fluorescence signal at the detection zone 31 with the fluorescence signal at the compensation zone 35, and optionally with the fluorescent signal at the calibration zone 32. For example, as indicated above, the amount of analyte may be determined by the ratio of $I_{det}/(I_{cal})(I_{com})$, and converting this ratio to an analyte concentration using a previously ascertained calibration curve.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes. Various assay formats may also be used to test for the presence or absence of an analyte using the assay device of the present invention. For instance, in the embodiment described above, a "sandwich" format is utilized. Other examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In addition, other formats, such as "competitive" formats, may also be utilized. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes.

The present inventor has discovered that the presence of a compensation zone on an assay device may enable the detection of an analyte over extended concentration ranges in a simple, efficient, and cost-effective manner. In particular, the compensation zone may compensate for the lost signals that would otherwise result from the limitations of optical detection techniques.

The present invention may be better understood with reference to the following examples.

Example 1

Conjugated fluorescent detection probes were formed in the following manner. Carboxylated latex particles were encapsulated with europium chelates having a particle size of 0.20 micrometers, a 0.5% solids concentration, and exhibiting fluorescence at an emission wavelength of 615 nanometers when excited at a wavelength of 370 nanometers. The particles were obtained from Molecular Probes, Inc. and designated as "Eu—P."

Initially, 500 microliters of the particles were washed once with 1 milliliter of a carbonate buffer and twice with 2-[N-morpholino]ethanesulfonic acid (MES) buffer (pH: 6.1, 20 millimolar) using a centrifuge. The washed particles were re-suspended in 250 microliters of MES. Thereafter, 3 milligrams of carbodiimide (Polysciences, Inc.) was dissolved in 250 microliters of MES and added to the suspended particles. The mixture was allowed to react at room temperature for 30 minutes on a shaker. The activated particles were then washed twice with a borate buffer (Polysciences, Inc) and re-suspended in 250 microliters of borate buffer. 30 microliters of C-protein monoclonal antibody (CRP Mab1) (3.4 milligrams per milliliter, A#5811 from BiosPacific, Inc.) was then added to the particle suspensions. The mixture was allowed to react at room temperature overnight on an end-over-end shaker. During the period of reaction, the suspensions were bath-sonicated twice. The particles were then collected and incubated in 250 microliters of 0.1 molar ethanolamine (Polysciences Inc.) under gentle shaking for 15 minutes. The particles were washed twice with hepes buffer (N-[2-hydroxyethyl]piperazine-N'-(2-ethanesulfonic acid) (20 millimolar, pH: 7.2). The washed conjugates were suspended in 1 milliliter of Hepes buffer and stored at 4° C.

Example 2

Conjugated fluorescent calibration probes were formed as described in Example 1, except that CRP Mab1 was replaced with Rabbit anti Goat IgG (Cat #41-RG15 from BiosPacific, Inc. Inc.) or Goat anti Rabbit IgG (Cat #41-GR30 from BiosPacific, Inc. Inc). The conjugated fluorescent calibration probes were designated as "Eu—P 41-RG15" and "Eu—P 41-GR30", respectively.

Example 3

The ability to form a lateral flow assay device with a detection zone and a compensation zone was demonstrated. A nitrocellulose porous membrane (HF 12002 from Millipore, Inc.) having a length of approximately 30 centimeters was laminated onto supporting cards. Goldline™ (a polylysine solution obtained from British Biocell International) was stripped onto the membrane to form a compensation zone. In addition, monoclonal antibody for C-reactive protein (CRP Mab2) (A#5804, available from BiosPacific, Inc., concentration of 1 milligram per milliliter) was immobilized on the porous membrane to form a detection zone. The membrane samples were then dried for 1 hour at a temperature of 37° C.

A conjugate pad was prepared as described below. 250 microliters of Eu—P CRP conjugated fluorescent detection particles of Example 1 (concentration of 2.5 milligrams per milliliter in Hepes buffer) was mixed with 375 microliters of Tween 20 (2%, available from Aldrich) and 375 microliters of sucrose in water (10%). The mixture was bath-sonicated for 20 minutes. The suspension was then loaded onto a 15-centimeter long glass fiber conjugate pad (Millipore Co.). The glass fiber pad was then dried at 37° C. for 2 hours.

A sample pad was prepared by loading 900 microliters of Tween 20 (0.5%) onto a 15-centimeter long glass fiber sample pad (Millipore Co.), and then drying the pad at 37° C. for 2 hours. A cellulose wicking pad (Millipore Co.), the sample pad, and conjugate pad were then laminated onto the porous membrane. The laminated full card was then cut into 4-millimeter wide lateral flow assay devices.

Example 4

The ability to detect the presence of an analyte using a lateral flow assay device was demonstrated. Specifically, eleven (11) of the assay devices prepared as described in Example 3 were tested. 55 microliters of diluted human blood (diluted by 100 times) was spiked with eleven (11) different CRP concentrations, ranging from 0, 0.2, 0.5, 1, 2, 10, 40, 100, 200, 500, and 2000 nanograms per milliliter, and applied to separate sample pads. The devices were allowed to develop for 30 minutes.

The fluorescence for the detection zone and calibration zone was measured. Specifically, upon completion of the assay, each lateral flow device was mounted onto a sample holder of a Fluorolog III Spectrofluorometer (available from SA Instruments, Inc.) using tape. The detection and compensation zones each fit into a rectangular hole in the holder so that the excitation beam would shine directly on the zone while the rest of the device was remained blocked from the excitation beam. Time-resolved fluorescence techniques were used. Specifically, the following experiment parameters were used: (1) the angle of the excitation beam to the surface normal of the devices was 70° C.; the detection mode was front face; the slit width was 5 nanometer; (4) the number of scan was 1; (5) the excitation wavelength was 370 nanometers; (6) the emission wavelength was collected at 615 nanometers; (7) the sample window was 3 milliseconds (ms); (8) the initial delay was 0.04 ms; (9) the time-per-flash was 50 ms; and (10) the number of flashes was 10.

The intensity at the detection zone for CRP concentrations of 0, 0.2, 0.5, 1, 2, 10, 40, 100, 200, 500, and 2000 nanograms per milliliter were determined to be 10.4K, 12.4K, 14.7K, 15.8K, 27.0K, 61.7K, 99.1K, 145.8K, 190.4K, 214.5K, 206.0K, respectively. The intensity at the compensation zone for CRP concentrations of 0, 0.2, 0.5, 1, 2, 10, 40, 100, 200, 500, and 2000 nanograms per milliliter was determined to be 280.9K, 216.3K, 165.0K, 187.5K, 170.0K, 123.7K, 65.4K, 56.0K, 8.2K, 3.9K, 2.3K, respectively. The intensity of the detection zone initially increased, but leveled off at a CRP concentration of about 200 to 500 nanograms per milliliter. The intensity of the compensation zone continued to decrease, even at a CRP concentration as high as 2000 nanograms per milliliter. Therefore, the ratio of the intensity at the detection zone to the intensity at the compensation zone would more accurately present the true CRP concentration for CRP concentrations higher than about 200 nanograms per milliliter.

Example 5

The ability to form a lateral flow assay device with a detection zone, a calibration zone, and a compensation zone was demonstrated. A nitrocellulose porous membrane (HF 12002 from Millipore, Inc.) having a length of approximately 30 centimeters was laminated onto supporting cards. Goldline™ (a polylysine solution obtained from British Biocell International) was stripped onto the membrane to form a compensation zone. Monoclonal antibody for C-reactive protein (CRP Mab2) (A#5804, available from BiosPacific, Inc., concentration of 1 milligram per milliliter) was immobilized on the porous membrane to form a detection zone. In addition, Rabbit anti prolactin antibody (A#5804, available from BiosPacific, Inc., concentration of 1.8 milligram per milliliter) was immobilized between the detection zone and the compensation zone on the porous membrane to form a calibration zone. The membrane samples were then dried for 1 hour at a temperature of 37° C.

250 microliters of the Eu—P CRP particles of Example 1 (concentration of 2.5 milligrams per milliliter in Hepes buffer) and 100 microliters of the Eu—P GR30 (2.5 milligrams per milliliter in Hepes buffer) particles of Example 2 were mixed with 300 microliters of Tween 20 (2%, available from Aldrich) and 300 microliters of sucrose in water (10%). The Eu—P CRP particles were used as detection probes, while the EU—P GR30 particles were used as calibration probes. The mixture was bath-sonicated for 20 minutes. The suspension was then loaded onto a 15-centimeter long glass fiber conjugate pad (Millipore Co.). The glass fiber pad was then dried at 37° C. for 2 hours.

A sample pad was prepared by loading 900 microliters of Tween 20 (0.5%) onto a 15-centimeter long glass fiber sample pad (Millipore Co.), and then drying the pad at 37° C. for 2 hours. A cellulose wicking pad (Millipore Co.), the sample pad, and conjugate pad were then laminated onto the porous membrane. The laminated full card was then cut into 4-millimeter wide lateral flow assay devices.

Example 6

The ability to detect the presence of an analyte using a lateral flow assay device was demonstrated. Specifically, nine (9) of the assay devices prepared as described in Example 5 were tested. 50 microliters of Hepes buffer was spiked with nine (9) different CRP concentrations, ranging from 0, 5, 20, 100, 500, 1000, 2000, 5000, and 10000 nanograms per milliliter, and applied to separate sample pads. The devices were allowed to develop for 30 minutes.

The time-gated fluorescence intensity was measured as described in Example 4, with the exception that the delay time was 0.04 milliseconds. The intensity at the detection zone for CRP concentrations of 0, 5, 20, 100, 500, 1000, 2000, 5000 and 10000 nanograms per milliliter was determined to be 26.7K, 39.0K, 47.0K, 109K, 159K, 186K, 217K, 219K, 193K, respectively. The intensity at the calibration zone for CRP concentrations of 0, 5, 20, 100, 500, 1000, 2000, 5000 and 10000 nanograms per milliliter was determined to be 96.6K, 136K, 101K, 119K, 103K, 88.7K, 86.8K, 88.1K, 87.9K, respectively. The intensity at the compensation zone for CRP concentrations of 0, 5, 20, 100, 500, 1000, 2000, 5000 and 10000 nanograms per milliliter was determined to be 123K, 146K, 93.6K, 158K, 131K, 81.8K, 69.3K, 54.1K, 34.0K, respectively. As indicated, the intensity at the detection zone initially increased, but then leveled off at a CRP concentration of about 2000 nanograms per milliliter, while the intensity at the compensation zone remained initially remained constant before beginning to decrease at a CRP concentration of about 1000 nanograms per milliliter. The intensity at the calibration zone remained relatively constant. Therefore, the ratio of the intensity at the detection zone to the intensity at the compensation zone, calibrated by the intensity at the calibration zone, would more accurately present the true CRP concentration for CRP concentrations of 2000 nanograms per milliliter or higher.

Example 7

The ability to form a half lateral flow assay device with a detection zone, a calibration zone, and a compensation zone was demonstrated. A nitrocellulose porous membrane (HF 12002 from Millipore, Inc.) having a length of approximately 30 centimeters was laminated onto supporting cards. Gold-line™ (a polylysine solution obtained from British Biocell International) was stripped onto the membrane to form a compensation zone. Monoclonal antibody for C-reactive protein (CRP Mab2) (A#5804, available from BiosPacific, Inc., concentration of 1 milligram per milliliter with 1 milligram of trehalose per milliliter) was immobilized on the porous membrane to form a detection zone. In addition, Rabbit anti prolactin antibody (A#5804, available from BiosPacific, Inc., concentration of 1.8 milligrams per milliliter) was immobilized between the detection zone and the compensation zone on the porous membrane to form a calibration zone. The membrane samples were then dried for 1 hour at a temperature of 37° C.

80 microliters of gold particles conjugated with Goat anti-Rabbit IgG (10 nanometer particle size, from Sigma) ("calibration probes") and 50 microliters of gold particles conjugated with CRP Mab1 (40 nanometer particle size, from British Biocell International) ("detection probes) were mixed with 280 microliters of water and 200 microliters of sucrose in water (10%). The suspension was then loaded onto a 10-centimeter long glass fiber conjugate pad (Millipore Co.). The glass fiber pad was then dried at 37° C. for 2 hours. A sample pad was prepared by loading 300 microliters of Tween 20 (0.5%) and 1200 microliters of water onto a 10-centimeter cellulose pad (Millipore Co.), then drying the pad at 37° C. for 2 hours. A cellulose wicking pad (Millipore Co.), the sample pad, and conjugate pad were then laminated onto the porous membrane. The laminated full card was then cut into 4-millimeter wide lateral flow assay devices.

Example 8

The ability to detect the presence of an analyte using a lateral flow assay device was demonstrated. Specifically, ten (10) of the assay devices prepared as described in Example 7 were tested. 60 microliters of Hepes buffer was spiked with ten (10) different CRP concentrations, ranging from 0, 5, 10, 20, 50, 100, 200, 500, 1000, and 2000 nanograms per milliliter, and applied to separate sample pads. The devices were allowed to develop for 30 minutes.

The reflectance intensity was measured using a reflectance reader. The reflectance intensity at the detection zone for CRP concentrations of 0, 5, 10, 20, 50, 100, 200, 500, 1000, and 2000 nanograms per milliliter was determined to be 0, 0, 0, 0.0498, 0.0806, 0.4433, 1.418, 2.347, 2.407, and 2.402, respectively. The reflectance intensity at the calibration zone for CRP concentrations of 0, 5, 10, 20, 50, 100, 200, 500, 1000, and 2000 nanograms per milliliter was determined to be 1.072, 0.9650, 0.9752, 1.010, 0.9993, 0.8954, 1.030, 1.020, 1.035, and 1.070, respectively. The intensity at the compensation zone for CRP concentrations of 0, 5, 10, 20, 50, 100, 200, 500, 1000, and 2000 nanograms per milliliter was determined to be 1.414, 1.167, 1.345, 1.312, 1.045, 1.241, 1.331, 0.843, 0.6169, and 0.4608, respectively. As indicated, the reflectance intensity at the detection zone initially increased, and then leveled off at about a CRP concentration of about 500 nanograms per milliliter, while the intensity at the compensation zone initially remained relatively constant before beginning to decrease at a CRP concentration of about 200 nanograms per milliliter. The intensity at the calibration zone remained relatively constant. Therefore, the ratio of the reflectance intensity at the detection zone to the intensity at the compensation zone, calibrated by the intensity at the calibration zone, would more accurately present the true CRP concentration for CRP concentrations of 500 nanograms per milliliter or higher.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flow-through assay device for detecting the presence or quantity of an analyte residing in a test sample, said flow-through assay device comprising a porous membrane, said porous membrane being in communication with detection probes and calibration probes, said detection probes having a net charge and being conjugated with a specific binding member for the analyte, said porous membrane defining:
   a detection zone within which is immobilized a first capture reagent, said first capture reagent being configured to bind to at least a portion of said conjugated detection probes or complexes formed between the analyte and said conjugated detection probes to generate a detection signal having an intensity;
   a compensation zone located downstream from said detection zone, wherein a polyelectrolyte is immobilized within said compensation zone, said polyelectrolyte having a net charge opposite to that of the detection probes, said polyelectrolyte being configured to bind to said conjugated detection probes and complexes formed between the analyte and said conjugated detection probes passing through said detection zone to generate a compensation signal having an intensity, wherein the intensity of said compensation signal is inversely proportional to the intensity of said detection signal; and
   a calibration zone within which a second capture reagent is immobilized, said second capture reagent being configured to bind to said calibration probes to generate a calibration signal that is substantially constant in intensity relative to the intensities of said detection signal and said compensation signal, said calibration zone being positioned between said detection zone and said compensation zone;
   wherein the amount of the analyte within the test sample is proportional to the ratio of said detection signal intensity to said compensation signal intensity, as calibrated by said calibration signal intensity.

2. A flow-through assay device as defined in claim 1, wherein said conjugated detection probes comprise a substance selected from the group consisting of chromogens, catalysts, luminescent compounds, radioactive compounds, visual labels, liposomes, and combinations thereof.

3. A flow-through assay device as defined in claim 1, wherein said conjugated detection probes comprise a luminescent compound.

4. A flow-through assay device as defined in claim 1, wherein said conjugated detection probes comprise a visual label.

5. A flow-through assay device as defined in claim 1, wherein said specific binding member is selected from the group consisting of antigens, haptens, aptamers, primary or secondary antibodies, biotin, and combinations thereof.

6. A flow-through assay device as defined in claim 1, wherein said first capture reagent is selected from the group consisting of antigens, haptens, protein A or G, neutravidin, avidin, streptavidin, captavidin, primary or secondary antibodies, and complexes thereof.

7. A flow-through assay device as defined in claim 1, wherein said polyelectrolyte has a net positive charge.

8. A flow-through assay device as defined in claim 7, wherein said polyelectrolyte is selected from the group consisting of polylysine, polyethyleneimine, epichlorohydrin-functionalized polyamines or polyamidoamines, polydiallyldimethyl-ammonium chloride, cationic cellulose derivatives, and combinations thereof.

9. A flow-through assay device as defined in claim 1, wherein said polyelectrolyte has a net negative charge.

10. A flow-through assay device as defined in claim 1, wherein said second capture reagent comprises antigens, haptens, protein A or G, neutravidin, avidin, streptavidin, captavidin, primary or secondary antibodies, or complexes thereof.

11. A flow-through assay device as defined in claim 1, wherein the device is a sandwich-type assay device.

12. A flow-through assay device as defined in claim 1, wherein the polyelectrolyte is ionically bonded to a functional group present on the surface of the porous membrane.

13. A flow-through assay device as defined in claim 1, wherein the polyelectrolyte is covalently bonded to a functional group present on the surface of the porous membrane.

14. A flow-through assay device as defined in claim 13, wherein the polyelectrolyte is crosslinked to the functional group.

15. A flow-through assay device as defined in claim 1, wherein the detection probes comprise latex microparticles.

16. A flow-through assay device as defined in claim 1, wherein the compensation zone is generally free of biological capture reagents.

17. A flow-through assay device as defined in claim 1, wherein said specific binding member includes an antibody.

18. A flow-through assay device as defined in claim 17, wherein said first capture reagent includes an antibody.

* * * * *